(12) United States Patent
Roeder

(10) Patent No.: US 9,763,817 B2
(45) Date of Patent: Sep. 19, 2017

(54) DELIVERY SYSTEM WITH CURVED PRELOADED CATHETER

(71) Applicant: Cook Medical Technologies LLC, Bloomington, IN (US)

(72) Inventor: Blayne A. Roeder, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 215 days.

(21) Appl. No.: 14/064,625

(22) Filed: Oct. 28, 2013

(65) Prior Publication Data

US 2014/0121749 A1 May 1, 2014

Related U.S. Application Data

(60) Provisional application No. 61/719,653, filed on Oct. 29, 2012.

(51) Int. Cl.
*A61F 2/06* (2013.01)
*A61F 2/954* (2013.01)
*A61F 2/962* (2013.01)
*A61F 2/07* (2013.01)

(52) U.S. Cl.
CPC ............... *A61F 2/954* (2013.01); *A61F 2/07* (2013.01); *A61F 2/962* (2013.01); *A61F 2002/061* (2013.01); *A61F 2002/065* (2013.01); *A61F 2230/0091* (2013.01)

(58) Field of Classification Search
CPC .. A61F 2/95; A61F 2/954; A61F 2/962; A61F 2/966; A61F 2/2427; A61F 2/2436; A61F 2002/9534
See application file for complete search history.

(56) References Cited

U.S. PATENT DOCUMENTS

| | | | |
|---|---|---|---|
| 4,552,554 A | 11/1985 | Gould et al. | |
| 4,774,949 A | 10/1988 | Fogarty | |
| 6,217,527 B1 | 4/2001 | Selmon et al. | |
| 6,302,875 B1 | 10/2001 | Makower et al. | |
| 6,379,319 B1 | 4/2002 | Garibotto et al. | |
| 6,514,217 B1 | 2/2003 | Selmon et al. | |
| 7,819,871 B2 | 10/2010 | Paul et al. | |
| 8,845,708 B2 | 9/2014 | Hartley et al. | |
| 2004/0220604 A1* | 11/2004 | Fogarty ............. | A61B 17/0218 606/190 |

(Continued)

FOREIGN PATENT DOCUMENTS

| | | |
|---|---|---|
| WO | WO 2004/067057 A2 | 8/2004 |
| WO | WO 2004/089249 A1 | 10/2004 |

(Continued)

OTHER PUBLICATIONS

European Communication and Search Report for corresponding EP 13275267 dated Nov. 21, 2014 (9 pages).

*Primary Examiner* — Melanie Tyson
(74) *Attorney, Agent, or Firm* — Brinks Gilson & Lione

(57) ABSTRACT

A delivery system for a medical device includes a proximal tip having a curved groove formed therein and a pre-loaded catheter disposed in the groove such that the pre-loaded catheter is disposed at least partly circumferentially with regard to the proximal tip. A guidewire can be advanced through the pre-loaded catheter and extended laterally from the delivery system.

20 Claims, 5 Drawing Sheets

(56) References Cited

U.S. PATENT DOCUMENTS

| | | | |
|---|---|---|---|
| 2008/0221656 A1* | 9/2008 | Hartley et al. | 623/1.11 |
| 2009/0105801 A1 | 4/2009 | Ivancev | |
| 2013/0131777 A1 | 5/2013 | Hartley et al. | |

FOREIGN PATENT DOCUMENTS

| | | |
|---|---|---|
| WO | WO 2007/059280 A1 | 5/2007 |
| WO | WO 2008/042270 A1 | 4/2008 |
| WO | WO 2008/109131 A2 | 9/2008 |
| WO | WO 2009/054971 A1 | 4/2009 |

* cited by examiner

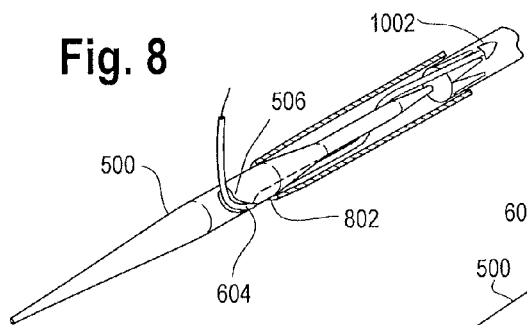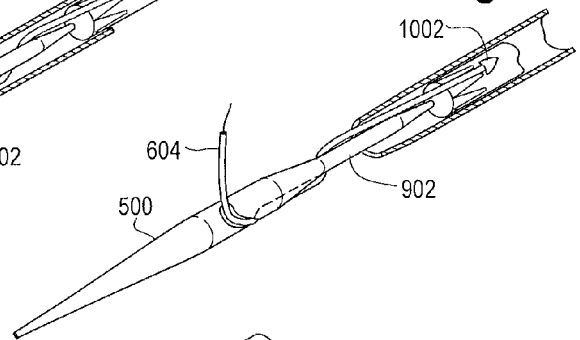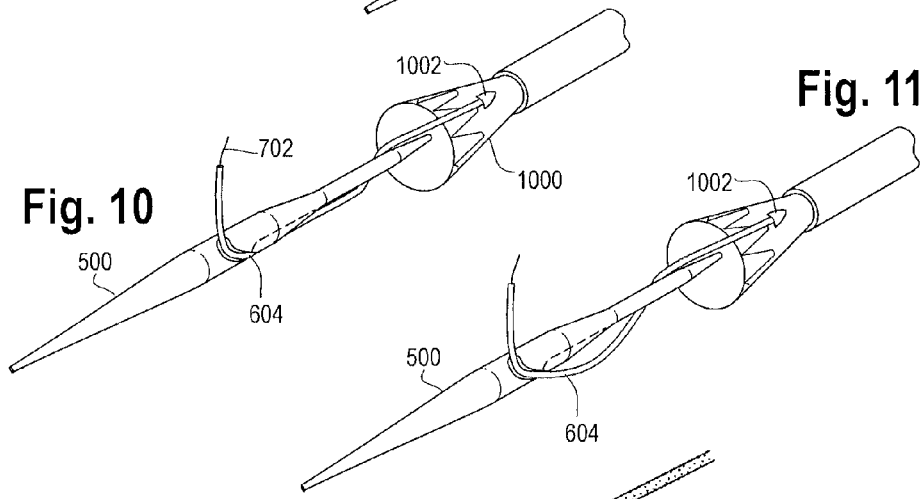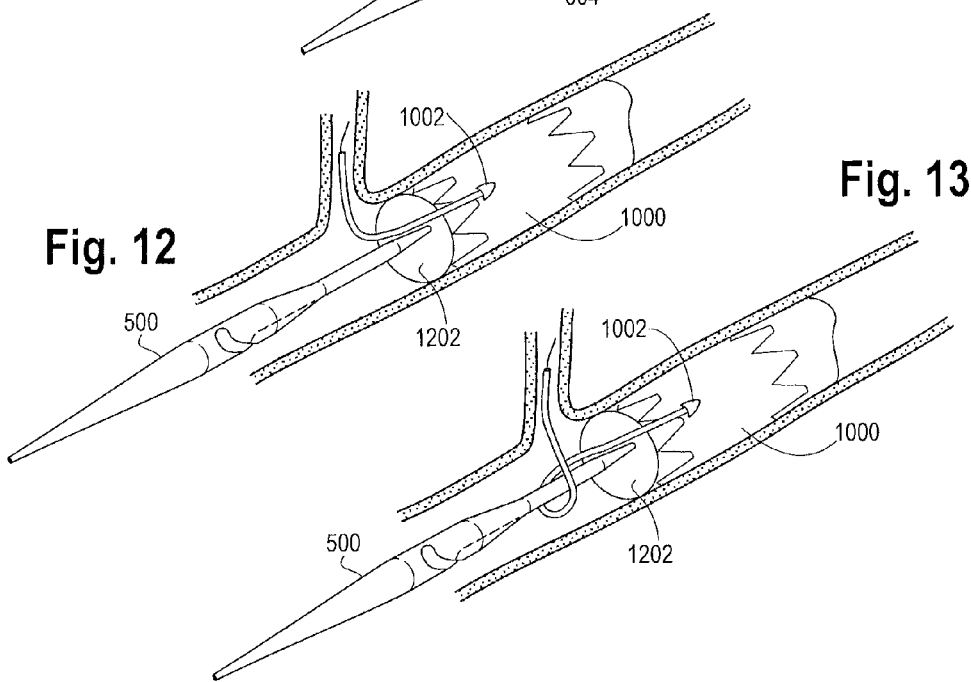

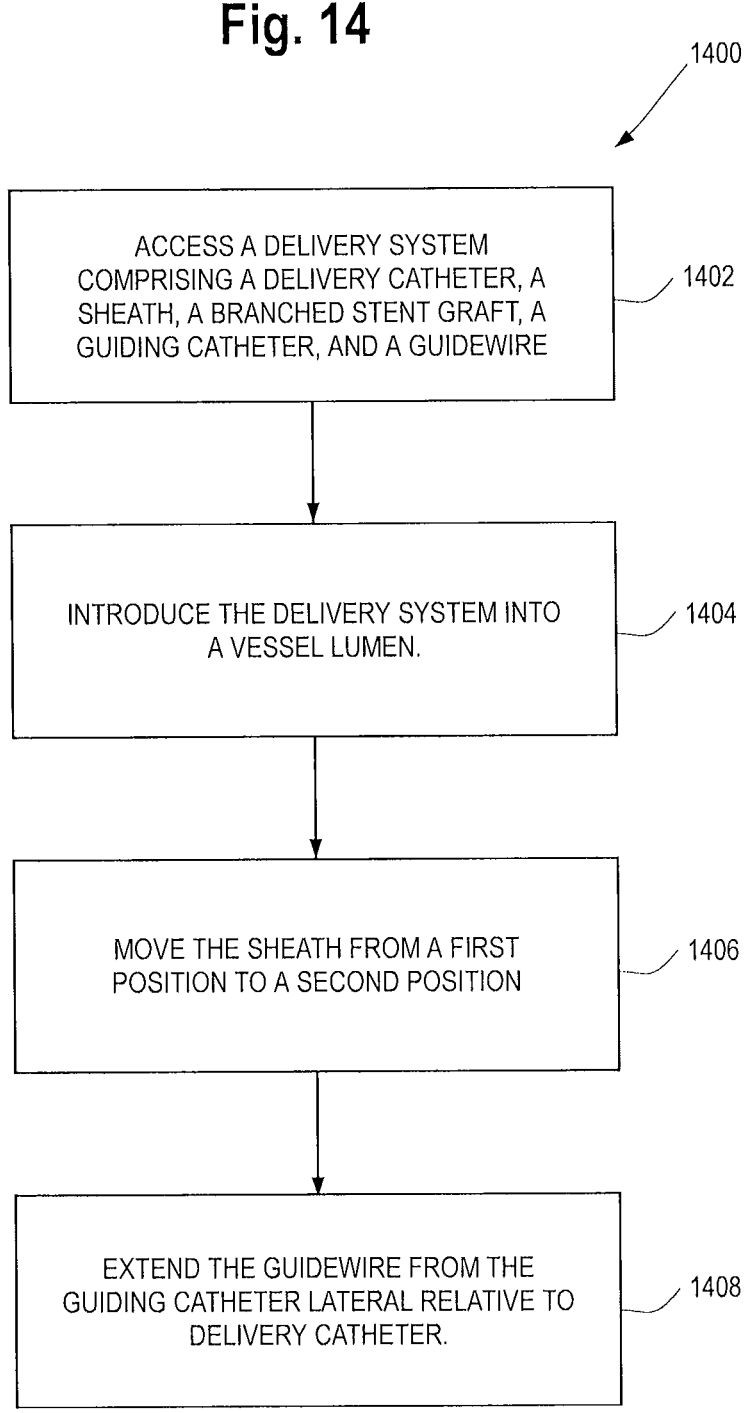

DELIVERY SYSTEM WITH CURVED PRELOADED CATHETER

CROSS-REFERENCE TO RELATED APPLICATIONS

This application is a non-provisional application which claims priority to U.S. Provisional Application No. 61/719,653 filed Oct. 29, 2012, the contents of which is incorporated in its entirety.

BACKGROUND

This invention relates to medical devices and, in particular, to devices, systems, and methods for delivery of a medical device into the human or animal vasculature by endovascular technique, and is particularly suited to deploying a stent graft where it may be necessary to catheterize a side branch vessel from a main vessel, for example, catheterizing the iliac artery from a contralateral iliac artery in order to deploy a stent graft. However, the invention is not limited to this example and may be utilized in any lumen where such catheterization is required.

Stent grafts are used to treat the vasculature in a human body or an animal body to repair or bypass a defect in the vasculature. For instance, a stent graft may be used to span an aneurism in an artery. In some instances, however, such a damaged or defective portion of the artery may include a branch vessel such as an internal iliac artery. A stent graft spanning the length of the aneurism may cause further complications if the stent graft does not provide blood flow into the branch vessel. To provide blood flow into the branch vessel, a side branch on a branched stent graft or fenestrated stent graft can be positioned over the opening to the side vessel and then another stent graft can be deployed through the side branch or the fenestration into the side vessel. Blood can then flow through the branched stent graft into the branch vessel through the side branch. Exemplary branched and fenestrated stent grafts, and their delivery systems are disclosed in U.S. Publication No. 2013-0131777, which is incorporated by reference herein in its entirety, and in particular FIGS. 1-23 and newly added FIG. 24 and the accompanying text. Further exemplary fenestrated stent grafts and their delivery system are disclosed in co-pending application Ser. No. 11/600,655, and in particular new FIGS. 9-12, which application is incorporated by reference herein in its entirety.

Using the Seldinger technique, a branched stent graft can be deployed into the common iliac artery by way of the femoral artery. During the positioning of the branched stent graft, it is necessary to align the side branch with the side vessel. A leg extension is then placed in the side vessel through the side branch. To align the branched stent graft and place the leg extension, it is beneficial to use a guidewire extending through the side branch and laterally into the side vessel.

Some systems and techniques to extend a guidewire laterally into the side vessel include a delivery system having the nose cone dilator shown in FIGS. 1 through 3. One example of such a system is shown in U.S. Publication No. 2009-0105801 A1, incorporated herein by reference in its entirety. In FIG. 1, the proximal end 100 of the delivery device is shown. The device includes a nose cone dilator 102 having a groove formed into the nose cone dilator 102. A curved pre-loading guiding catheter 106 and a guide-wire 108 (shown in FIG. 3). The curved guiding catheter 106 is disposed in a groove 104 formed into the nose cone dilator 102 and is biased to extend laterally such that its natural position directs the guidewire 108 in a specific direction (e.g., toward the contralateral iliac for an iliac branch device). The guide-wire 108 can then be extended laterally through the curved guiding catheter 102 when the nose cone dilator 102 is in place, thereby facilitating snaring the guidewire and a creating a through-wire for device alignment and/or facilitating the delivery of a bridging stent. As shown, a retractable sheath 110 is disposed over a portion of the dilator tip.

In FIG. 1, the curved guiding catheter 106 is not constrained and extends from the nose cone dilator 102 during sterilization and shipping. This allows the curved guiding catheter 106 to retain its curved shaped following sterilization and storage. If the curved guiding catheter 106 were to be constrained to a straight shape during sterilization and shipping, there is a potential that the curved guiding catheter 106 could lose its curved shape.

As shown in FIG. 2, when the delivery system is ready for use, the sheath 110 is advanced over the curved guiding catheter 106 to constrain the curved guiding catheter 106 such that it no longer extends outside of the sheath 110. If the curved guiding catheter 106 were to remain extended from the nose cone dilator 102 during delivery, it is possible that the curved guiding catheter 106 could be damaged or interfere with the guidance of the delivery system.

Once the device is delivered to the desired treatment site as shown in FIG. 3, the sheath 110 is retracted distally and the curved guiding catheter 106 returns to its natural shape extending laterally from the nose cone dilator 102. The guidewire 108 can then be extended laterally.

Preparing such a delivery system requires at least one additional step. Because the proximal most part of the guiding catheter must retain its curved shape, at least part of it must protrude from the main body tip outside of the sheath for shipping and storage. This ensures that the pre-formed curve will be maintained. Hence prior to inserting the delivery system, the sheath 110 must be advanced over the curved guiding catheter 106 tip to completely sheath it. As described above, the delivery system cannot be packaged with the sheath 110 restraining the curved guiding catheter 106, as the curved guiding catheter 106 may lose its shape over time. Furthermore, the curved tip must be re-sheathed so that it is protected as it advances through the body vessel.

SUMMARY

Embodiments of the present invention provide for a delivery system for a medical device. In one embodiment, the delivery system includes a first catheter, a nose cone dilator, and a second catheter. The first catheter has a distal end, a proximal end, and a longitudinal axis. The nose cone dilator is disposed at the proximal end of the first catheter and has a groove formed on an outer surface of the nose cone dilator. The groove may have a distal portion parallel to the longitudinal axis and a proximal portion extending circumferentially about the outer surface. The groove may be helical or substantially helical. The second catheter has a proximal end and a distal end. The second catheter proximal end is constrained within the groove and extends from the distal portion of the groove to the proximal portion of the groove. The second catheter is pre-loaded in the delivery system and is part of the delivery system as introduced into a patient.

In another example, a delivery system includes a delivery catheter, a sheath, and a pre-loaded guiding catheter. The delivery catheter has a proximal tip and a longitudinal axis.

A groove is disposed on an exterior surface of the proximal tip and the groove has a distal portion parallel to the longitudinal axis and a proximal portion extending circumferentially about the outer surface. The sheath is disposed about a portion of the delivery catheter and at least partially over the groove and is slidable in a longitudinal direction relative to the delivery catheter from a first position to a second position. The guiding catheter extends a length of the delivery catheter and is constrained within the groove by the sheath in the first position.

The invention also includes a method of delivering a guidewire including accessing a delivery system, introducing the delivery system into a vessel lumen, moving the sheath from the first position to the second position, and extending the guidewire from the guiding catheter lateral relative to the delivery catheter. The delivery system accessed includes a delivery catheter having a proximal tip, a groove disposed in a surface of the proximal tip, the groove having a distal portion parallel to a longitudinal axis of the catheter and a proximal circumferential portion, a sheath covering the groove, the sheath movable from a first position covering the groove to a second position at which a proximal portion of the groove in uncovered, a fenestrated stent graft disposed between the sheath in the first position and the delivery catheter, the fenestrated stent graft having a side branch, a guiding catheter extending from the side branch into the proximal portion of the groove, and a guidewire disposed in the guiding catheter.

BRIEF DESCRIPTION OF THE DRAWINGS

To further clarify the above and other advantages and features of the one or more present inventions, reference to specific embodiments thereof are illustrated in the appended drawings. The drawings are exemplary and therefore not to be considered limiting.

FIG. 8 depicts an exemplary nose cone dilator with a properly positioned curved guiding catheter.

FIG. 9 depicts an exemplary nose cone dilator with an improperly positioned curved guiding catheter.

FIG. 10 depicts a partially deployed branched stent with a properly positioned curved guiding catheter.

FIG. 11 depicts a partially deployed branched stent with an improperly positioned curved guiding catheter.

FIG. 12 depicts a deployed branched stent with a properly positioned curved guiding catheter.

FIG. 13 depicts a deployed branched stent with an improperly positioned curved guiding catheter.

FIG. 14 depicts a flow chart of a method for placing a guidewire in a delivery system.

DETAILED DESCRIPTION

In the present application, the term "proximal" refers to a direction that is generally closest to the heart during a medical procedure, while the term "distal" refers to a direction that is furthest from the heart during a medical procedure. For further clarity, in the present case, the proximal end of the device is that part that is inserted into a patient and the distal end is that part that remains outside of the patient.

The term "stent" means any device or structure that provides, or is configured to provide, rigidity, expansion force, or support to a body part (e.g., a diseased, damaged, or otherwise compromised body lumen.). A stent may comprise any suitable material, including, but not limited to, biocompatible metals and plastics. Examples of suitable materials include metals such as stainless steel and NITINOL, and plastics such as polyethylene terephthalate ("PET"), polytetrafluoroethylene ("PTFE") and polyurethane.

A stent may be "expandable," that is, it may be capable of being expanded from a constricted configuration to an expanded configuration. A stent may be self-expanding and expand by virtue of its own resilience. Alternatively, a stent may be pressure-expandable and expand only upon the application of an external force. In addition, a stent may be expandable upon application of heat, such as when exposed to body temperature. An example of a self-expanding stent is the Z-STENT®, which is available from Cook Incorporated, Bloomington, Ind., USA.

The term "lumen" describes a cavity or channel within a tube or a tubular body, such as body vessel. The term "endoluminal" means within a lumen, and can refer to objects that are found or that can be placed within a lumen, or methods or processes that occur within a lumen.

The term "pre-loaded" means in place in the delivery system prior to use of the device on the patient.

Figure 1:
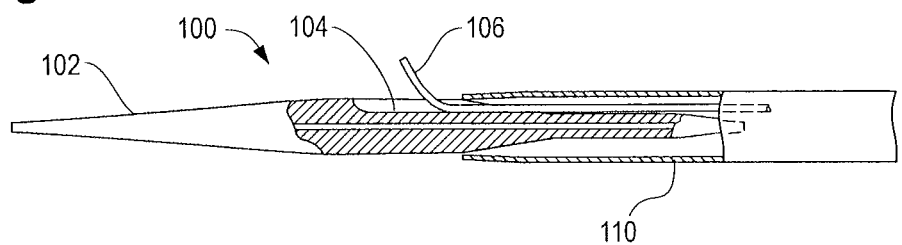
FIG. 1 depicts a nose cone dilator of a delivery system as packaged for shipping with a curved guiding catheter and a retracted sheath.
Figure 2:
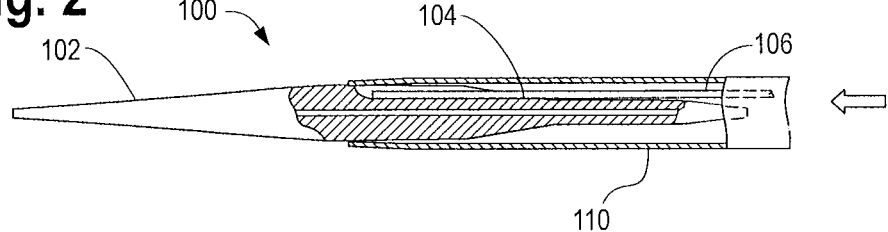
FIG. 2 depicts the nose cone dilator of FIG. 1 for insertion into a vessel with the sheath advanced to restrain and completely cover the curved guiding catheter.
Figure 3:
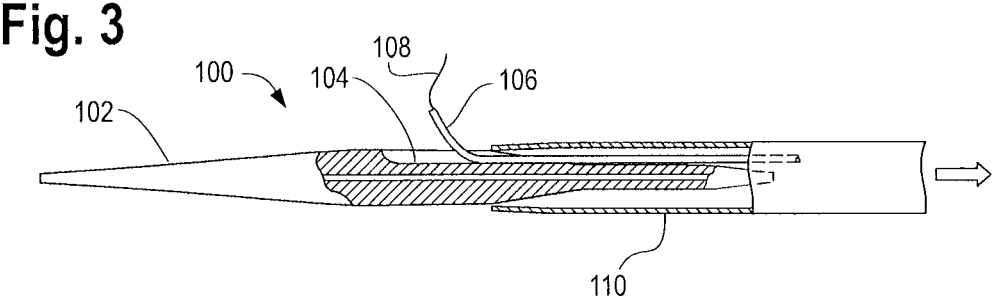
FIG. 3 depicts the nose cone dilator of FIG. 1, post-delivery, with the sheath retracted allowing the curved guiding catheter to extend laterally.
Figure 4:
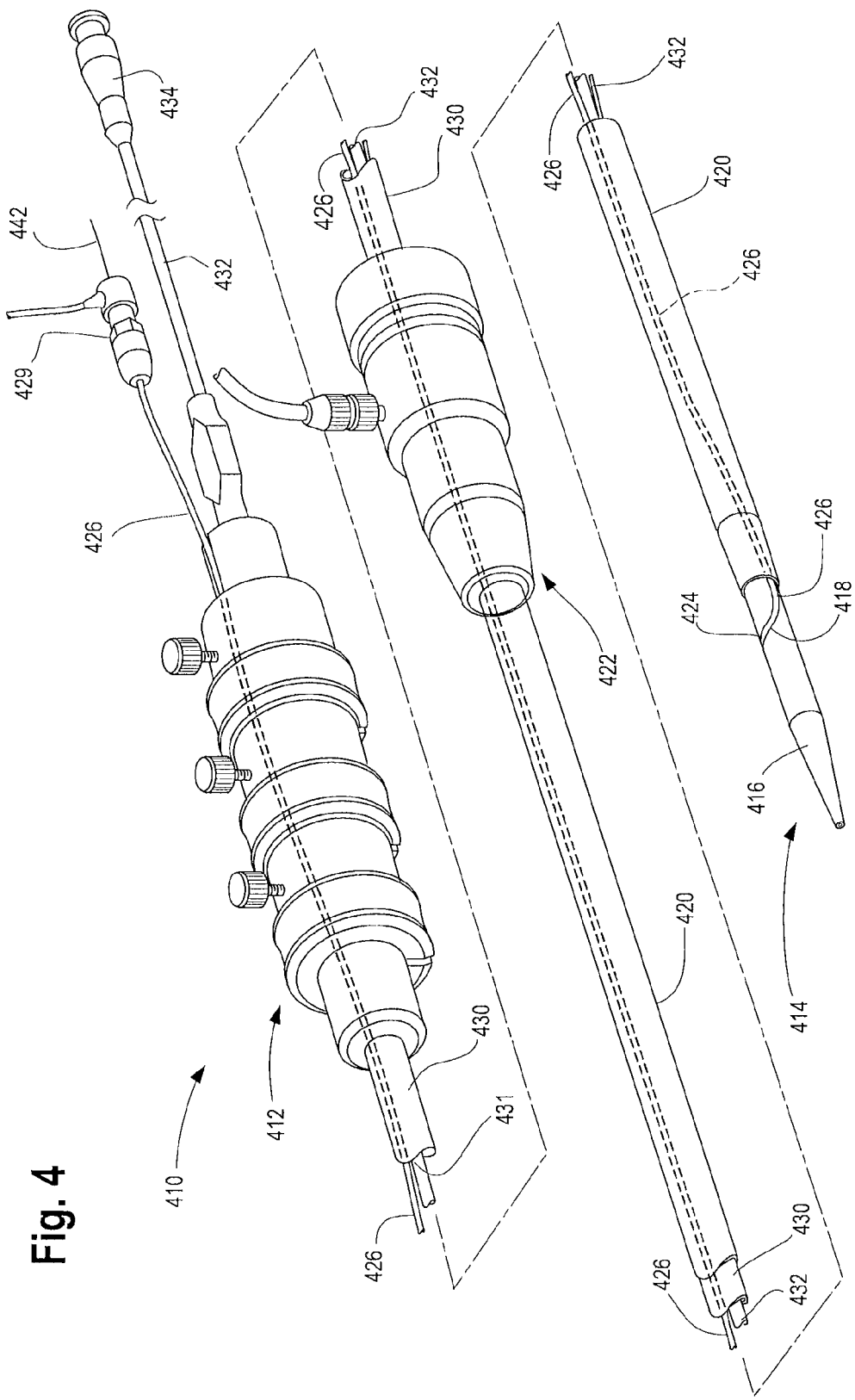
FIG. 4 depicts an exemplary delivery system for a stent graft prosthesis.

Turning to FIG. 4, a delivery system 410 is shown. The delivery system 410 includes a handle portion 412 and a deployable portion 414 which is deployed into a patient during an endovascular procedure. The deployable portion 414 comprises a nose cone dilator 416 with a curved groove 418 formed on its outer surface. A sheath 420 extends from a sheath hub 422 to the nose cone dilator 416. In FIG. 4, the sheath 420 has been partially retracted by retraction of the hub 422 to show a curved tip 424 of a guiding catheter 426.

The guiding catheter 426 extends from the nose cone dilator 416 to a hemostatic seal 429 adjacent to the handle 412 of the delivery system 410. The guiding catheter 426 extends through a hemostatic seal 429 within the handle 412 and a lumen 431 of a delivery catheter 430. The lumen 431 extends through the guiding catheter 426 so that an auxiliary guidewire 442 may be deployed there through. The delivery catheter 430 extends from the handle 412 through the hub 422 and terminates distally of the nose cone dilator 416. A main guidewire catheter 432 extends from a syringe hub 434 through the rear of the handle 412 through the lumen 431 of the delivery catheter 430 to the nose cone dilator 416.

Proceeding distally along the length of the delivery system 410, the guiding catheter 426 extends through the lumen 431 in the delivery catheter 430 and then extends out of the rear of the handle 412.

Figure 5:
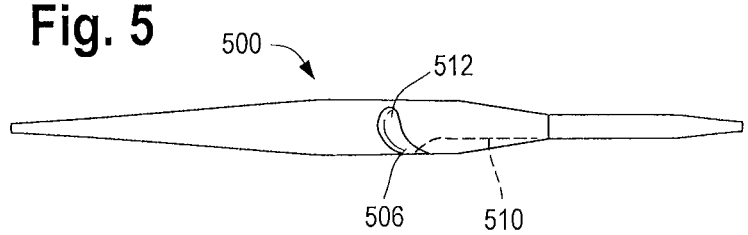
FIG. 5 depicts an exemplary nose cone dilator having a curved groove for receiving a curved guiding catheter.

FIG. 5 depicts a nose cone dilator 500 having a curved groove 506 for receiving a guiding catheter (not shown). The curved groove 506 is disposed in the outer surface of the nose cone dilator 500. A distal end 510 of the curved groove 506 is substantially parallel to a longitudinal axis of the nose cone dilator 500. A proximal end 512 of the curved groove 506 extends at least partially circumferentially about the outer surface and may be orthogonal to the longitudinal axis. In some embodiments, the curved groove 506 follows a path similar to a portion of a helix as it extends around the surface of the nose cone dilator 500. The curved groove 506 may be substantially "U" shaped in cross section to receive a guiding catheter (not shown). The curved groove 506 shapes the guiding catheter to have a longitudinal orientation at the distal end 510 of the curved groove 506 to a circumferential orientation 506 at the proximal end 510 of the groove. The curved groove 506 has a bottom surface that extends outward to join the outer surface of the nose cone dilator 500.

Figure 6:
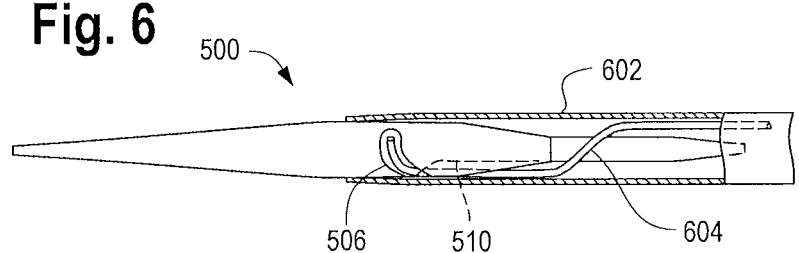
FIG. 6 depicts the nose cone dilator of claim 5 with the curved guiding catheter received in the curved groove.

FIG. 6 depicts the nose cone dilator 500 of FIG. 5 with a retractable sheath 602 in place over the curved groove 506. A guiding catheter 604 is disposed in the curved groove 506 between the nose cone dilator 500 and the retractable sheath 602. In this state, the delivery system is ready to be packaged with the guiding catheter 604 in place, constrained from movement by the retractable sheath 602. Because the curved groove 506 is curved complementary to the curve of the guiding catheter 604, there is not a danger of the guiding catheter 604 losing its curve during packaging and sterilization.

The delivery system may be introduced into a vascular system with the nose cone dilator 500 in the configuration shown in FIG. 6. In contrast to the conventional delivery systems described previously, there is no need for a user to first advance the sheath 602 over the guiding catheter 604, since the delivery system is packaged with the guiding catheter 604 already sheathed. The delivery system is introduced in a vessel in this state and guided to a deployment location.

Figure 7:
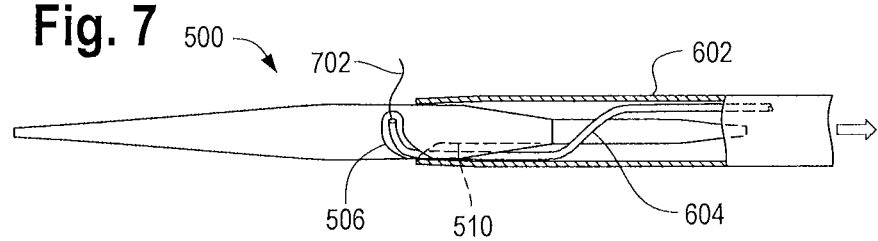
FIG. 7 depicts the nose cone dilator of claim 5 with a guidewire extending laterally from the nose cone dilator.

Once the delivery system is in place at the deployment location, the user may partially retract the retractable sheath 602. FIG. 7 illustrates the nose cone dilator 500 with the retractable sheath 602 partially retracted once the delivery system in place. In FIG. 7 the retractable sheath 602 is partially retracted such that the proximal portion 512 of the curved groove 506 is uncovered, thereby exposing the guiding catheter 604. A guidewire 702 is shown exiting the guiding catheter 604 in a direction extending away from the longitudinal axis of the delivery system in a circumferential direction. Since no constraint is provided to the guidewire 702 once it exits the guiding catheter 604, the guidewire 702 extends straight laterally from the delivery system. The delivery system may be rotated to position the guiding catheter 604 at a desired orientation. In embodiments in which the delivery system has a sufficient torsional rigidity, the distal end of the delivery system may be rotated to orient the guiding catheter 604. In some embodiments, the delivery system may be auto orientating such that the guiding catheter 604 naturally aligns to a predicable location. For example, a curved cannula in an arch would auto align a general curve of the cannula with a curve of the arch. In some embodiments, the guiding catheter 604 may extend substantially orthogonal to the longitudinal axis of the delivery system. The guiding catheter 604 may remain in the curved groove 506 while the guidewire 702 is extended from the guiding catheter 604. The partially retracted retractable sheath 604 may cover the distal portion of the groove constraining the guiding catheter within the groove. Because the extension of the guidewire 702 may occur without any movement by the guiding catheter 604, the guidewire 702 may be extended even if the delivery system is against a vessel wall.

However, if the guiding catheter 604 is placed in the curved groove 506 improperly, the guiding catheter 604 may wrap around the delivery system and cause complications. FIG. 8 illustrates the proper placement of the guiding catheter 604. In FIG. 8, a distal portion 802 of the guiding catheter 604 is on the same side of the nose cone dilator 500 as the curved groove 506. FIG. 9 illustrates improper placement of the guiding catheter 604. In FIG. 9, a distal portion 902 of the guiding catheter 604 is opposite the curved groove 506 of the nose cone dilator 500.

FIG. 10 illustrates the delivery system with the sheath (not shown) partially retracted such that a stent graft 1000 is partially expanded. The guiding catheter 604 exits the stent graft 1000 through a side arm 1002 and curves away from the axis of the nose cone dilator 500. The guidewire 702 exits the guiding catheter 604 and extends away from the delivery system. FIG. 11 illustrates the delivery system with the improperly positioned guiding catheter 604 of FIG. 9. Once again, the sheath (not shown) is partially retracted allowing the stent graft 1000 to expand partially. The guiding catheter 604 exits the stent graft 1000 through the side arm 1002 and wraps around the nose cone dilator 500. The guiding catheter 604 then extends away from the axis of the nose cone dilator 500. The guidewire 702 exits the guiding catheter 604 like in FIG. 10; however, the guiding catheter 604 and guidewire 702 are wrapped around the nose cone dilator 500. While the end result is the guidewire 702 extending laterally from the delivery system as intended, the sharpened radius of curvature of the guiding catheter 604 makes it difficult to extend the guidewire 702, and as will be shown in FIG. 13, and may cause additional complications.

In FIG. 12, a fully deployed branched stent 1000 is illustrated. The nose cone dilator 500 exits out a main lumen 1202 of the branched stent 1000, while the guiding catheter 604 and guidewire 702 exit the branched stent 1000 through the side branch 1002. A user can now guide a leg extension (not shown) through the side branch 1002 and into position in the side vessel. FIG. 13 illustrates an improperly positioned guiding catheter 604 that wraps around the nose cone dilator 500 disrupting the path from the side branch 1002 to the side vessel. If the guiding catheter 604 is positioned incorrectly as in FIGS. 9, 11, and 13, a leg extension likely cannot be guided into the side vessel through the branched stent 1000.

FIG. 14 is a flow chart illustrating a method 1400 of introducing a guidewire. The method begins with block 1402 wherein a user accesses a delivery system. The delivery system includes a delivery catheter having a proximal tip, a groove disposed in an exterior surface of the proximal tip, the groove having a distal portion parallel to a longitudinal axis of the delivery catheter and a proximal circumferential portion, a sheath covering the groove, the sheath movable from a first position covering the groove to a second position at which a proximal portion of the groove is uncovered, and a branched stent graft disposed between the sheath in the first position and the delivery catheter, the branched stent graft having a side branch, a guiding catheter extending from the side branch into the proximal portion of the groove, and a guidewire disposed in the guiding catheter. Examples of the delivery system being accessed by the user include when a user opens a package containing the delivery system, a user assembling the delivery system, the delivery system being assembled for the user, or any other act that results in the user accessing the delivery system. For example, block 1402 may include a user opening a package containing the delivery system 410 of FIG. 4.

In block 1404, the user introduces the delivery system into a vessel lumen. For example, a user may introduce the delivery system 410 of FIG. 4 into a femoral artery of a patient. In some embodiments, the user may cause the delivery system to be introduced into a vessel lumen. For the purposes of this application, if the user is in control of the delivery system being introduced into a vessel lumen, it will be understood that this is the equivalent of the user introducing the delivery system into a vessel lumen.

In block 1406, the user partially retracts the sheath of the delivery system exposing a portion of the guiding catheter. Again, a user will be considered to have partially retracted the sheath if the user is in control of the retraction of the sheath. Referring to FIG. 4, a user may retract the sheath hub 422 causing the sheath 420 to partially retract exposing a portion of the groove.

With the sheath partially retracted, the user can then extend the guidewire laterally from the catheter as indicated in block 1408. Referring again to FIG. 4 for example, the user may advance guidewire 442 at the distal portion of delivery system 410 causing the guidewire 442 to extend from the guiding catheter 426. When the guidewire 442 is extended, the guiding catheter 426 will generally remain within the groove due to the constraint provided by the partially retracted sheath 420. As such, the guidewire 442 is able to extend without movement of the guiding catheter 426. In situations where a vessel wall is proximate the proximal tip 416 of the delivery system, the guidewire 442 may still be extended despite any interference between the vessel wall and the catheter.

The method may further include fully retracting the sheath 420 to expose the groove in its entirety. For example, referring to FIG. 4, the user may further retract the sheath hub 422 causing the sheath 420 to retract further thereby fully exposing the groove. The sheath 420, once fully retracted, no longer constrains the guiding catheter 426 within the groove and the guiding catheter 426 may then be released from the groove.

As discussed above, the stent graft may be a fenestrated stent graft such as that shown in application Ser. No. 11/600,655, FIGS. 9-12, which application is incorporated by reference herein in its entirety and in particular FIGS. 9-12. As shown in application Ser. No. 11/600,655, FIGS. 9 and 10, a pre-loaded catheter may extend along side the exterior surface of a fenestrated stent graft, enter the lumen of the fenestrated stent graft through a fenestration in a side wall of the stent graft and exit the proximal end of the stent graft. As shown, the pre-loaded catheter is curved. Prior to deployment the proximal end of the pre-loaded catheter resides within the curved or helical grove in the nose cone dilator and is covered by the sheath as described in that application. As shown in FIGS. 11 and 12 of application Ser. No. 11/600,655, the pre-loaded catheter enters the fenestrated stent graft at the distal end, extends out of the fenestration and toward the proximal end of the delivery device. As shown, the pre-loaded catheter is curved. Prior to deployment the proximal end of the pre-loaded catheter resides within the curved or helical grove in the nose cone dilator and is covered by the sheath as described in that application and here. In further embodiments, the stent graft may have more than one fenestration, and/or one or more side branches. The term "fenestration" may include an opening through which a side branch stent graft may be placed, and may also refer to a side branch that is integral with the stent graft and/or removably attached thereto. In one example, the stent graft may have at least two fenestrations. In such a case, each fenestration is provided with its own pre-loaded catheter. The pre-loaded catheters accommodate guide wires to cannulate respective vessel branches, such as the renal arteries. Thereafter, a separate branch stent graft may be delivered via a separate delivery system through each of the fenestrations and into the branch vessel. FIG. 24 of U.S. publication no. 2013-0131777 (FIG. 24 added after publication of that application) exemplifies a fenestrated stent graft system with a separately added side branch. This FIG. 24 is specifically incorporated herein by reference in its entirety.

Throughout this specification, the invention has been described in relation to a delivery catheter and a guiding catheter, but the invention is not limited to these particular catheters. Additionally, various indications have been given as to preferred and alternative embodiments of the invention. However, it should be understood that the invention is not limited to these embodiments. It is therefore intended that the foregoing detailed description be regarded as illustrative rather than limiting.

What is claimed is:

1. A delivery system for a medical device comprising:
   a first catheter having a distal end, a proximal end, and a longitudinal axis;
   a nose cone dilator disposed at the proximal end of the first catheter, the nose cone dilator having a curved groove formed in an outer surface of the nose cone dilator, the curved groove having a distal portion parallel to the longitudinal axis and a proximal portion extending from the distal portion and circumferentially about the outer surface in a continuous curvilinear path from the distal portion through the proximal portion; and
   a second catheter, pre-loaded in the delivery system, and having a proximal portion and a distal portion, the second catheter proximal portion being disposed in at least the proximal portion of the curved groove and extending from the proximal portion of the curved groove to the distal portion of the curved groove, such that the second catheter proximal portion is curved complementary to the continuous curvilinear path of the proximal portion of the curved groove such that the distal portion of the second catheter lies within the distal portion of the curved groove and the proximal portion of the second catheter lies in the proximal portion of the curved groove.

2. The delivery system of claim 1 further comprising:
   a sheath disposed about the nose cone dilator proximate the curved groove, wherein the second catheter is constrained within the curved groove by the sheath.

3. The delivery system of claim 1 wherein the curved groove is at least partially helical.

4. The delivery system of claim 1 wherein the curved groove has a bottom surface that extends to the outer surface of the nose cone dilator.

5. The delivery system of claim 1 further comprising:
   a branched stent graft retained on the proximal end of the first catheter and having a stent graft lumen and a side branch extending from the stent graft between the proximal and distal ends of the stent graft.

6. The delivery system of claim 5 wherein the side branch is aligned with the distal portion of the curved groove.

7. The delivery system of claim 5 wherein the side branch is aligned with the proximal portion of the curved groove.

8. The delivery system of claim 5 wherein the second catheter extends through the stent graft lumen and through the side branch to the nose cone dilator.

9. The delivery system of claim 1 wherein the proximal portion of the curved groove is substantially perpendicular to the longitudinal axis.

10. The delivery system of claim 1 further comprising:
a fenestrated stent graft retained on the delivery catheter, the fenestrated stent graft having proximal end, a distal end and a fenestration disposed between the proximal end and the distal end, where the second catheter is disposed through the fenestration.

11. A delivery system for a medical device comprising:
a delivery catheter having a proximal tip and a longitudinal axis;
a curved groove disposed in an exterior surface of the proximal tip, the curved groove having a distal portion parallel to the longitudinal axis and a proximal portion extending circumferentially about the proximal tip, wherein the proximal portion of the curved groove extends from the distal portion of the curved groove in a continuous curvilinear path;
a sheath disposed at least partially over the proximal tip and the curved groove, the sheath slidable in a longitudinal direction relative to the delivery catheter from a first position to a second position; and
a pre-loaded guiding catheter extending a length of the delivery catheter and disposed in the curved groove, such that the second catheter is curved complementary to the continuous curvilinear path of the curved groove through the distal and proximal portions of the curved groove.

12. The delivery system of claim 11 further comprising a branched stent graft disposed on the delivery catheter and within the sheath, and having a proximal end and a distal end, the branched stent graft having a lumen and a side branch extending from the stent graft between the proximal end and the distal end.

13. The delivery system of claim 12 wherein the pre-loaded guiding catheter extends from the side branch into the distal portion of the curved groove.

14. The delivery system of claim 11 wherein the curved groove has a bottom surface that extends to the outer surface of the proximal tip.

15. The delivery system of claim 11 wherein the guiding catheter is constrained within the curved groove with the sheath in the second position exposing a portion of the curved groove.

16. The delivery system of claim 11 further comprising:
a fenestrated stent graft retained on the delivery catheter, the fenestrated stent graft having proximal end, a distal end and a fenestration disposed between the proximal end and the distal end, where the pre-loaded guiding catheter is disposed through the fenestration.

17. A method of delivering a guidewire comprising:
accessing a delivery system comprising:
a delivery catheter having a proximal tip;
a curved groove disposed in a surface of the proximal tip, the curved groove having a distal portion parallel to a longitudinal axis of the catheter and a proximal circumferential portion extending from the distal portion to form a continuous curvilinear path from the distal portion through the proximal portion;
a sheath covering the curved groove, the sheath movable from a first position covering the curved groove to a second position at which a proximal portion of the curved groove is uncovered;
a fenestrated stent graft disposed between the sheath and the delivery catheter, the fenestrated stent graft having a side branch extending from the fenestrated stent graft between a proximal end and distal end of the fenestrated stent graft;
a guiding catheter extending from the side branch into the proximal portion of the curved groove, wherein the guideing catheter is curved complementary to the continuous curvilinear path of the curved groove; and
a guidewire disposed in the guiding catheter;
introducing the delivery system into a vessel lumen;
moving the sheath from the first position to the second position exposing a portion of the curved groove and guiding catheter; and
extending the guidewire from the guiding catheter lateral relative to the delivery catheter.

18. The method of claim 17 wherein the guiding catheter remains at least partially in the curved groove when the sheath is moved to the second position.

19. The method of claim 17 wherein the guiding catheter remains at least partially in the curved groove when the guidewire is extended from the guiding catheter.

20. The method of claim 17 wherein the second position releases the fenestrated stent graft.

* * * * *